United States Patent [19]
Lyman et al.

[11] 4,173,689
[45] Nov. 6, 1979

[54] SYNTHETIC POLYMER PROSTHESIS MATERIAL

[75] Inventors: Donald J. Lyman; Frank J. Fazzio, both of Salt Lake City, Utah

[73] Assignee: University of Utah, Salt Lake City, Utah

[21] Appl. No.: 654,831

[22] Filed: Feb. 3, 1976

[51] Int. Cl.$^2$ .......................... C08G 18/14; A61F 1/24
[52] U.S. Cl. ............................................. 521/64; 3/1; 3/1.4; 3/1.7; 260/30.8 DS; 260/32.6 NR; 264/41; 428/315; 428/425
[58] Field of Search .................... 264/41; 3/1, 1.4, 1.7; 260/2.5 A, 2.5 AD, 2.5 AY, 2.5 M; 428/315; 521/64

[56] References Cited

U.S. PATENT DOCUMENTS

| | | | |
|---|---|---|---|
| 2,540,906 | 2/1951 | Overton et al. | 264/49 X |
| 3,449,153 | 6/1969 | Saligny | 260/2.5 AY |
| 3,483,015 | 12/1969 | Fukushima | 260/2.5 AY |
| 3,512,183 | 5/1970 | Sharp | 3/1.4 |
| 3,555,129 | 1/1971 | Fukada | 260/2.5 M |
| 3,622,526 | 11/1971 | Zorn | 260/2.5 AY |
| 3,644,233 | 2/1972 | Traubel | 260/2.5 AY |
| 3,664,979 | 5/1972 | Tanomura | 260/2.5 AY |
| 3,700,380 | 10/1972 | Kitrilakis | 3/1 |
| 3,720,631 | 3/1973 | Fukushima | 260/2.5 AY |
| 3,743,530 | 7/1973 | Oohara | 260/2.5 AY |
| 3,803,061 | 4/1974 | Fabre | 260/2.5 M |
| 3,853,462 | 12/1974 | Smith | 3/1.4 |
| 3,862,452 | 1/1975 | Wichterle | 3/1.4 |
| 4,010,494 | 3/1977 | Sauer | 3/1 |
| 4,021,382 | 5/1977 | Stoy | 260/2.5 M |

*Primary Examiner*—H. S. Cockeram
*Attorney, Agent, or Firm*—Criddle, Thorpe & Western

[57] ABSTRACT

A blood and body-tissue compatible synthetic polymer having mechanical compliance properties matching that of body tissue, useful in prosthesis as vascular grafts, skin covering, small diameter body duct work, and similar tissue replacement materials. A block copolymer having suitable body and blood compatibility characteristics is dissolved in a solvent, yielding a solution having an approximate relative viscosity between the range of 100 to 1000. A clean mandrel is slowly dipped into the solution and slowly withdrawn, leaving a uniform coating of polymer solution over the forming surface of the mandrel. The coated mandrel is then immersed into a second, nonsolvent solution which is miscible with the first solvent. The resulting transfer of the nonsolvent solution into the polymer network, displacing the first solvent molecules, acts to precipitate the polymer in a physical form containing a uniform dispersion of voids throughout the polymer structure. Such voids provide a mechanical response to the final polymer material which parallels that of natural arterial tissue, while at the same time retaining the necessary compatibility characteristics for prosthesis.

22 Claims, 1 Drawing Figure

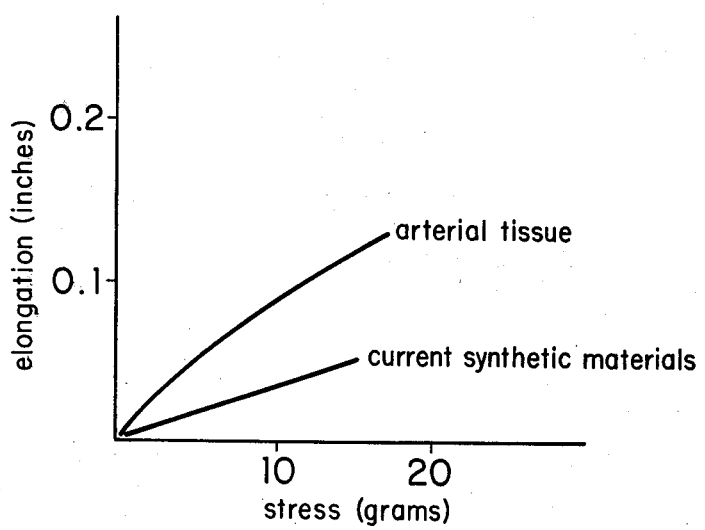

SYNTHETIC POLYMER PROSTHESIS MATERIAL

The Government has rights in this invention pursuant to Grant No. GH 38996 X awarded by the National Science Foundation.

BACKGROUND

The utility of synthetic polymers as replacement material for various types of human tissue has been substantially advanced by recent developments in improved compatability characteristics of polymer compositions with the numerous chemical environments of the body. Although improvements in body tissue and blood compatibility (hereinafter referred to as "compatibility") have enabled more extensive use of synthetic polymers in prosthetic surgery, the continued failure of many of these implants has greatly impeded progress in treatment of persons requiring replacement of human tissue.

It has now been discovered that many of these failures were the product of mechanical mis-match, as well as compatability rejection. Inasmuch as the effects of these two causes are quite similar—clotting of the blood and tissue rejection—the subsequent failure of the newer nonthrombogenic materials was viewed as simply a further rejection due to other chemically adverse reactions to the prosthetic implant.

Recent investigation of vascular grafts has disclosed, however, that such thrombosis and accompanying graft failure of these nonthrombogenic materials was the result of mechanical mis-match between the graft and natural tissues. Such mis-match includes a variance in elastic response and other physical properties such that the grafted material does not mechanically respond in consonance with the natural tissue. The resulting traumatization and other adverse tissue reactions cause clotting and occlusion of the vein, similar to that experienced with chemical noncompatibility.

These effects of compliance mis-match are particularly troublesome in small diameter vascular grafts. The continual variations of blood pressure cause a recurring pulsing motion resulting in constant expansion and contraction of the vascular tissues. Where the grafted material is not of an equivalent compliance with the natural vascular tissue, the inconsonant response of the grafted portion results in fluid turbulence and direct tissue damage at the sutured juncture. If the diameter of the fluid path is large or if the rate of fluid flow is high, the adverse effects of thrombosis may not be severe. This is true, for example, in the larger vessels such as the aorta which has both large diameters and substantial blood flow. If, however, these favorable conditions are not present, blood clots accumulate and frequently result in occlusion of the fluid path. For this reason, none of the previous grafts (polymer, Dacron, or ceramic) have been effective in the venous side of the circulatory system or where the vessel diameter has been less than 6 mm on the arterial side. The combination of minimal diameter and/or reduced blood flow have precluded the effective use of synthetic material for such vascular grafts.

Because of the unavailability of suitable synthetic materials with the required compliance characteristics, vascular grafts for small diameter blood vessels now require the transplantation of saphenous vein from the leg of the patient or other vein material from the less critical parts of the circulatory system. This procedure is limited, however, due to potential risks of resultant circulation failure, particularly in older persons. Furthermore, it is not uncommon for an older patient to have failing saphenous veins, requiring the use of potential donors with the accompanying risks of antigenic reactions. The seriousness of these limitations is illustrated by the fact that approximately 60% of the amputations currently performed in hospitals are the result of vascular failure.

Similarly, rejection of prosthetic materials in other body systems has been commonly experienced. Frequently, the treatment of such areas as the common bile duct, urethra, ureta and hydrocephalic tubes includes the need of tissue replacement which has previously been unsuccessful due to the concurrent needs of compatibility and mechanical compliance. Such requirements are not satisfied by synthetic materials now available in the commercial market.

The seriousness of compliance mis-match is more clearly illustrated by examining the graph depicted in the FIGURE, which compares the elasticity of current prosthetic materials with that of the natural artery tissue.

It should be noted that there is a substantial difference in elongation response between the compared materials. This variance becomes even more acute in the body environment where the forces to which mechanical response is required are often small. Consequently, synthetic polymers which appear to be sufficiently elastic when being manually stretched, will give little response to very slight pressures which occur in the body. Unless the prosthesis material has mechanical properties matching such tissue to which it is to be connected, there will be an adverse reaction tending toward rejection of the material.

SUMMARY AND OBJECTIVES OF THE INVENTION

It is therefore an object of the present invention to provide a synthetic material having mechanical compliance with body tissue.

It is a further object of the present invention to provide a mechanically compliant synthetic material having blood and body tissue compatibility characteristics suitable for prosthesis use.

It is an additional object of this invention to provide a synthetic material with compatibility and compliance characteristics suitable for prosthesis use, having a reinforced structure to ensure safety and long life.

It is still a further object of this invention to provide a mechanically compliant synthetic material having blood and body compatibility characteristics suitable for prosthesis use, being adaptable for use as surgical graft, replacement material or covering for numerous types of organic tissue.

It is another objective of this invention to provide such a prosthesis material having suitable characteristics to facilitate suturing or methods of attachment to the subject area of treatment.

It is still another object of the present invention to provide a usable method for fabrication of the aforementioned materials, such method being to produce a polymer product having a variety of mechanical compliance characteristics suitable for various types of tissue prosthesis.

The fabrication of a blood and body-tissue compatible polymer into a suitable form having elasticity and similar physical properties matching the compliance of human tissue is accomplished by a unique process of forming a uniform dispersion of voids within a suitable polymer such as block copolyurethanes. The resultant sponge-like structure allows elastic deformation upon such slight stress as that experienced by vascular tissue due to variations of blood pressure. Such voids are formed by dissolving the polymer in a suitable solvent (ie. N,N-dimethylformamide for block copolyurethanes) to form a solution of moderate viscosity. A clean forming device such as a mandrel or other suitable surface configuration is slowly immersed into the viscous solution and then slowly withdrawn, leaving a solution coating on the mandrel comprising the viscous polymer with a uniform dispersion of solvent molecules throughout the polymer network. The voids are introduced by displacing these solvent molecules with nonsolvent molecules which act to precipitate the polymer into a stable physical structure.

This process of displacement involves the critical balance between the rates of transfer of solvent material out of the polymer network and a concurrent transfer of precipitating solution into the space formerly occupied by the solvent molecules. As a consequence, the precipitating polymer does not experience substantial shrinkage, but retains a physical network structure with a uniform dispersion of precipitating solution throughout the solidified material. The precipitating solution is then removed and the resulting cavities or voids within the polymer structure create a spongy texture having the necessary elasticity to match tissue compliance requirements. By repeating this procedure the thickness of polymer coating can be increased and material compliance adjusted to a less elastic response if desired.

To add strength and control the direction of elasticity of the precipitated polymer, a knitted fabric having high elongation in the appropriate directions can be placed over the product of the first precipitation process and then a second coat procedure is conducted to enclose the fabric within the final product. Additional applications may be useful to adjust the degree of compliance to match the tissue to which the graft will be made.

DETAILED DESCRIPTION

This invention deals with the use of block copolymers having compatibility with blood and body tissues. This general class of copolymers has shown potential utility in various prosthesis applications, but has been heretofore limited to where compliance mis-match has not created a serious problem. The development of a highly elastic form of compatible synthetic polymers requires a technique that produces a product which retains the compatibility characteristics unique to only certain structural arrangements of the polymer chains while at the same time modifying the physical form of such polymers to include a uniform dispersion of voids or small air pockets which cause the desired elasticity.

Although other polymers of the general class of block copolymers may be equally susceptible to the precipitation process outlined herein, the specific subclass of copolyurethanes has been utilized because of their potential for many types of prosthetic applications. Specifically, the copolyurethanes are formed by the reaction of a prepolymer such as polyether diols with diisocyanates, with the resultant product being chain extended by the reaction of a diol or diamine as a coupling agent. Such a polymerization process produces copolymers having the preferred molecular weight and viscosity. Copolyetherurethane-ureas and copolyetherurethanes are representative of the types of block copolymers that would be adaptable to the precipitation process outlined herein.

To achieve successful precipitation of the final material, the block copolymer starting material should have a molecular weight represented by an inherent viscosity between the range of 0.4 to 1.0 as measured in a viscosimeter using a solution of 0.5% concentration in N,N-dimethylformamide at 30° C. Molecular weights represented by a viscosity lower than 0.4 result in mechanical failure of the final material upon subjection to strain. If the polymer molecular weight is excessively large (greater than 1.0 viscosity) the polymer dipping solution becomes unworkable due to its extreme viscosity.

It will be noted, therefore, that the critical factor in selecting an appropriate starting material is a determination that the length of the polymer chain (represented by the inherent viscosity) must be sufficient to meet the potential mechanical strains to which the product will be subjected, yet small enough to preserve the desired viscosity characteristics of the final polymer solution. The range of 0.4 to 1.0 inherent viscosity is an experimental approximation of the molecular size limitations.

Preparation methods for block copolymers having potential utility for the proposed precipitation process are available in the current state of the art. The synthesis of copolyether-urethane of suitable molecular weight, for example, is discussed in Lyman, D. J., "The Development and Implantation of a Polyurethane Hemispherical Artificial Heart", Trans. Amer. Soc. Artif. Int. Organs, 1971, Vol 17, p. 456.

The block copolymer starting material is dissolved in a suitable nonadverse solvent such as sulfoxide type solvents (i.e. dimethyl sulfoxide) or amide type solvents (i.e. N,N-dimethylformamide) and the resulting dipping solution is filtered to ensure freedom from foreign material. The amount of solvent used is adjusted to yield a resulting solution having a percent solids between 5–12% and a relative viscosity ($\eta_{rel}$) between 100 to 1000 at the temperature at which the fabrication is conducted. This relative viscosity is calculated in accordance with the following formula:

$$\eta_{rel} = (t/t_o)$$

where t=flow time of the solution and $t_o$=flow time of the solvent.

The critical element in this process is to achieve a final dipping solution viscosity and percent solids which will result in the application of a proper thickness and texture of polymer coating to the mandrel or other forming device. The following table illustrates various suitable viscosities of the polymer solution as a function of the percent concentration of the copolymer at 30° C.

|    | Polymer Conc. | Relative Viscosity ($\eta$) rel at 30° C. |
|----|---------------|-------------------------------------------|
| 1. | 7%            | 160                                       |
| 2. | 9%            | 555                                       |
| 3. | 10%           | 992                                       |

Precipitations from the above solutions have produced usable final products having the desired compatibility and compliance characteristics.

By raising the temperature of more concentrated solutions, the resultant decrease in viscosity may permit precipitation of suitable polymers from solution concentrations of higher percentages, provided the relative viscosity does not exceed the indicated approximate range limits of 100 and 1000 and the rates of solvent and nonsolvent exchange aren't adversely effected. Although the temperature range for the copolyurethane class of block copolymers may be varied from approximately 10° C. to 60° C., the best precipitation conditions appear to be at approximately 9% concentration of the polymer in N,N dimethylformamide at 30° C.

Once the appropriate concentration and viscosity of the dipping solution are obtained, a clean mandrel or other forming device is slowly immersed therein in such a manner as to prevent adverse air bubble entrapment. The mandrel is slowly withdrawn from the solution at a uniform rate to ensure an even coating of polymer solution over the desired surface of the forming device. The mandrel is then immersed in a suitable precipitating solution to fix the polymer structure without causing the excessive shrinkage of polymer material such as results from the normal "solution coating" processes where the solvent is allowed to evaporate so as to form the final material.

Processes not accompanied by the displacing step of substituting precipitating nonsolvent molecules for the nonprecipitating solvent molecules dispersed throughout the polymer solution coating, fail to develop the necessary elastic characteristic. Usually, such processes yield a material of substantially less thickness than the original solution coating because the final hardening process relies on the removal of solvent out of the polymer network without the concurrent replacement with a precipitating molecule. The polymer molecules fill in the vacancies, thus collapsing the polymer into a more dense form.

By displacing the solvent molecule of the dipping solution with a second non-solvent molecule, however, the shrinkage of the polymer coating is limited. If this same substituted molecule has the effect of precipitating the polymer molecules into their existing structure at the time of displacement, the polymer coating becomes fixed and the mandrel may be removed from the precipitating solution without disturbing the form of the final polymer structure. This displacing process may be accomplished by any solution (herein referred to as the nonsolvent or precipitating solution) which possesses the necessary chemical properties of (1) suitable precipitating effect on the polymer network to fix the structure prior to removal from the precipitating solution, and (2) miscibility of the solvent and nonsolvent molecules.

$H_2O$ has been demonstrated as very effective for the displacement of the amide and sulfoxide type solvents from copolyurethane solutions. The coated mandrel or forming device is immersed in the $H_2O$ immediately after removal of the mandrel from the dipping solution. The polymer material is retained in the $H_2O$ until infusion thereof into the polymer-solvent mixture. This time period may vary with the viscosity of the polymer solution, however 15 to 60 minutes is usually sufficient depending upon whether the material is the final product or whether additional coatings are to be applied.

Additives or rate impeding constituents may be used to impede displacement of solvent molecules and thereby adjust the extent of void formation within the precipitated polymer. These additives may be placed directly in the polymer solution or in the water-nonsolvent solution. These additives include carbowax ketones and inorganic salts and their use may permit greater control of the balance between solvent extraction and nonsolvent absorption.

After the polymer structure is precipitated by the displacement of solvent by $H_2O$, the mandrel is removed and allowed to dry at an approximate temperature range of 25° to 85° C. in a suitable environment (air, inert gas, etc.). The resultant precipitated product possesses a uniform dispersion of voids throughout the material which renders the polymer structure mechanically suitable for prosthetic use. The elastic response of this precipitated product essentially parallels that of natural arterial tissue, thereby resolving compliance mis-match.

Not only does this process result in excellent compliance matching with tissue, but the subject precipitation method preserves the necessary surface structure of the polymer network to preserve compatibility characteristics for prosthetic use. Current methods for forming copolyurethanes such as "solution coating" can develop polymer surfaces of varying compatibility response depending upon factors such as solvent, drying rate, mold versus air side exposure of film, etc. These surface differences have been shown to cause differences in biological response of tissue. The proposed precipitate process, however, appears to allow the polymer to retain its best surface characteristics.

Once the original material is dried, additional coatings may be added prior to removal from the forming device to adjust to the desired compliance and other physical needs, such as suturability. Furthermore, mechanical strength may be enhanced by the encapsulation of fiber material within the precipitated material. This is accomplished by covering the precipitated first layer of polymer material with any suitable fabric having the desired elongation and strength characteristics. A jersey knit type structure has been successfully utilized in preparing vascular grafts having the necessary radial elongation properties for compliance matching.

The resultant product of the precipitation process is a blood and body-tissue compatible copolymer whose mechanical compliance may be adjusted to match various tissues within the body. Such synthetic materials have been produced which mechanically respond in essentially the same manner as body vascular tissue. The harmoneous operation of such grafts has been evidenced by the natural pulsing motion of the graft in the actual circulation system of test animals. Such grafts have been successfully implanted in dogs whose rate of thrombosis is much higher than that of human systems. Under identical test conditions, grafts utilizing current commercial materials have experienced immediate failure and resultant occlusive thrombosis due primarily to compliance mis-match.

Potential uses of the precipitated polymer are foreseeably extensive. In addition to signficant application in vascular graft treatment, the material may be utilized for prosthesis treatment of stomach and bladder tissue, as well as for prosthetic nerve cuff material. The replacement of small diameter duct work of the body is another major medical application having specific utility in urethra, ureta, common bile duct and similar prostheses. The precipitated polymer may be formed in sheets and applied as a skin covering in burn treatment or for other skin covering applications. Additional uses may develop where the prosthesis requirements include the mutual elements of compatibility and mechanical compliance. This method of precipitation permits fabrication of numerous shapes and forms by varying the surface configuration of the forming device utilized in the precipitation process.

We claim:

1. A method of fabricating a prosthesis material for use with a living body, said prosthesis having mechanical properties of compliance and elasticity approximating that of soft body tissue and being operable to preserve surface properties of blood and tissue compatibility, said method comprising the steps
   (a) preparing a copolyurethane composition having a molecular weight range approximately corresponding to an inherent viscosity of 0.4 to 1.0 as measured in a solution of 0.5% concentration in N,N-dimethylformamide at 30° C.;
   (b) dissolving an amount of said copolyurethane composition in solvent to produce a dipping solution having 5-12% by weight polymer concentration, said solution having a relative viscosity between the range of 100 to 1000 at a dipping temperature of 10° C. to 60° C.;
   (c) coating forming means with a uniform thickness of said dipping solution; and
   (d) precipitating said coating into a stable physical structure having a substantially uniform dispersion of voids throughout the copolyurethane composition by immersing said coated forming means into a precipitating solution comprising a fluid which is miscible in said solvent but operable as a precipitating nonsolvent with respect to the said copolyurethane composition, the precipitation being accomplished by means of a balanced rate of exchange between said solvent and nonsolvent molecules which prevents any substantial shrinkage of said coating during precipitation and fixes said copolyurethane composition in a stable physical structure.

2. A method as defined in claim 1 wherein the selected block copolymer is taken from the group consisting of copolyether-urethanes and copolyether-urethane ureas.

3. A method as defined in claim 1, wherein the solvent is selected from the group consisting of sulfoxide solvents and amide solvents.

4. A method as defined in claim 3 wherein the solvent is selected from the group consisting of dimethyl sulfoxide and N,N-dimethylformamide.

5. A method as defined in claim 1 wherein the precipitating nonsolvent is $H_2O$.

6. A method as defined in claim 1, wherein the precipitating step is regulated by controlling the rate of exchange between said solvent and nonsolvent molecules by adding rate impeding constituents to the polymer solution of step b or to the nonsolvent material of the precipitating step.

7. A process as defined in claim 6 wherein said rate impeding constituents are selected from the group consisting of polyethylene glycols, ketones and inorganic salts.

8. A method as defined in claim 1, wherein an additional step comprises drying the precipitated copolyurethane composition.

9. A blood and tissue compatible, synthetic prothesis material prepared in accordance with the method defined in claim 1, wherein said material has mechanical properties of compliance and elasticity approximating those of organic tissue.

10. A product as defined in claim 9, wherein the copolyurethane is selected from the group comprising copolyether-urethanes and copolyether-urethane ureas.

11. A prosthesis material as defined in claim 9, wherein the material is configured as a nerve cuff.

12. A prosthesis material as defined in claim 9, wherein the material is formed in a sheet structure suitable for protective or prosthesis application for skin.

13. A prosthesis duct formed in accordance with the method defined in claim 1.

14. A prosthesis duct as defined in claim 13, wherein the duct is adapted for replacement of human tissue selected from the group consisting of urethra, ureta and common bile duct tissue.

15. A prosthesis duct as defined in claim 13 having an inner diameter of approximately 6 mm or less.

16. A vascular graft formed in accordance with the method defined in claim 1.

17. A vascular graft as defined in claim 16, wherein the graft has an inner diameter of 6 mm or less.

18. A process for replacing soft body tissue comprising the steps of:
   (a) Preparing prosthesis material fabricated in accordance with the method of claim 1, and
   (b) applying said material to a portion of a living body to form an integral combination of prosthesis material and living tissue.

19. A process as defined in claim 18, wherein the prosthesis material is formed in a structure substantially equivalent to natural vascular tissue.

20. A process as defined in claim 19, wherein the prosthesis material is sutured to natural vascular tissue to form a continuation thereof.

21. A process as defined in claim 18, wherein the prothesis material is structured in duct configuration substantially equivalent to duct tissue of a living body.

22. A process as defined in claim 21, wherein the prosthesis material is attached to form part of a ureta, urethra or bile duct within a living body.

* * * * *